United States Patent
Dungan

(10) Patent No.: US 6,252,510 B1
(45) Date of Patent: Jun. 26, 2001

(54) APPARATUS AND METHOD FOR WIRELESS GAS MONITORING

(76) Inventor: Bud Dungan, 21104 Halburton Rd., Beachwood, OH (US) 44122

(*) Notice: Subject to any disclaimer, the term of this patent is extended or adjusted under 35 U.S.C. 154(b) by 0 days.

(21) Appl. No.: 09/333,352

(22) Filed: Jun. 15, 1999

Related U.S. Application Data

(60) Provisional application No. 60/104,223, filed on Oct. 14, 1998, and provisional application No. 60/122,863, filed on Mar. 4, 1999.

(51) Int. Cl.[7] .................................................. G08B 17/10
(52) U.S. Cl. .......................... 340/632; 340/539; 73/31.02
(58) Field of Search ..................................... 340/632, 633, 340/634, 539, 521, 601, 602; 73/23.2, 31.01–31.03

(56) References Cited

U.S. PATENT DOCUMENTS

| | | | |
|---|---|---|---|
| 5,132,968 | 7/1992 | Cephus | 370/94.1 |
| 5,406,265 | * 4/1995 | Trozzo et al. | 340/632 |
| 5,446,445 | * 8/1995 | Bloomfield et al. | 340/521 |
| 5,481,181 | 1/1996 | McHardy et al. | 324/71.1 |
| 5,822,373 | * 10/1998 | Addy | 375/259 |
| 5,861,316 | 1/1999 | Cage et al. | 436/52 |
| 6,114,964 | * 9/2000 | Fasano | 340/632 |

OTHER PUBLICATIONS

Gas Detection Systems Inc., publication entitled "Turn–Key Wireless Gas Detection", published prior to Oct. 14, 1998.
Gas Detection Systems, Inc. publication entitled "Stackpac", published prior to Oct. 14, 1998.
Gas Detection Systems, Inc. publication entitled "GDS–2000 Teledetection System", published prior to Oct. 14, 1998.
B & W Technologies Ltd. publication entitled "Wireless Multi–point Gas Monitoring–Rig Rat", published prior to Oct. 14, 1998.
Photographs (2) of Georgia Gulf Corporation installation in Louisiana prior to Oct. 14, 1998. Printing designating various components of the installation has been added to the photographs.

* cited by examiner

Primary Examiner—Jeffery Hofsass
Assistant Examiner—Sihong Huang
(74) Attorney, Agent, or Firm—Tarolli, Sundheim, Covell, Tummino & Szabo L.L.P.

(57) ABSTRACT

The current invention discloses a wireless monitoring system. The system has one or more monitoring devices. Each device can transmit data to and receive messages from an output center or alarm system. The output center can also transmit and receive messages. Both the output center and each device preferably have a transceiver that enables both the transmission and receipt of messages. No remote terminal units or hardwiring is required for the system to function. The system is truly a wireless gas monitoring system. The system may use low earth orbit satellite technology, or licensed radio frequencies or any other means to wirelessly transmit and receive messages.

3 Claims, 6 Drawing Sheets

APPARATUS AND METHOD FOR WIRELESS GAS MONITORING

This application claims the benefit of U.S. Provisional Application No. 60/104,223 filed Oct. 14, 1998 and U.S. Provisional Application No. 60/122,863 filed Mar. 4, 1999.

BACKGROUND OF THE INVENTION

I. Field of the Invention

This invention relates to the field of gas monitoring. The invention provides a method and apparatus for wireless monitoring of gases, including toxic and combustible gases, with a device that has a radio transmitter that transmits quantitative gas levels to a master controller or multiple master controllers.

II. Description of the Related Art

Toxic gas monitoring systems are well known. Generally, gas monitors are placed around chemical producing facilities such as a chemical processing plant. These monitoring systems are configured to monitor for the presence of toxic and/or combustible chemicals. In addition to monitoring for the presence these chemicals, typically in parts per million or lower explosive limits, these detectors can also detect other important information such as wind speed and direction, temperature and other weather conditions. This information is then relayed to some sort of output system. For instance, the information can be relayed back to the control center of a chemical plant and be displayed on a computer terminal or be comprised in a computer printout.

Conventional toxic gas monitoring systems comprise multiple sensing units. These units are placed around the perimeter of a chemical processing plant, for example, to constantly monitor the conditions around the plant. Upon detection of a toxic gas, usually at a predetermined level, the unit may sound an alarm in addition to relaying the information to the control center. This information can be used, for example, to determine the source of the gas so that an unexpected leak can be corrected. Alternatively, should the plant simply be operating at too high of a capacity and thus be generating too much toxic waste, its operations can be brought to within acceptable tolerances. Additionally, the wind speed, weather conditions and direction of the gas can be used to determine which people need to be warned about the presence of toxic gas and when such a warning should be issued.

Typically, in gas detection systems a master site provides information to a computer. U.S. Pat. Nos. 5,553,094, 5,568,121 and 5,771,004 disclose such systems. U.S. Pat. No. 5,597,534 discloses a circuit that measures a chemical sensor output. Typically, specially designed software is incorporated as well. For example, the Gastronics' Event Scada Software is an unlimited tag Scada software which runs off Windows '95 or Windows NT and is designed for user friendliness along with the ability to customize and map out the geography of a plant. The Event Scada Software offers the user the flexibility to design and customize individual screens to match different applications. An assortment of tools allows the creation of trend charts, wind speed and direction, alarm settings and maintenance screens. A multilevel security feature may be included to prevent unauthorized access to customization functions.

Currently, the method of relaying this important information from the monitors to the control center has been through wires which physically connect each of the monitors to the output system. This is generally referred to as "hard wiring." Hard wiring requires each monitor to be physically connected to the output system by some sort of wire or cable. Hard wiring each of the numerous monitors to the control system can be quite costly, cumbersome and require substantial and frequent maintenance. For example, should the output system ever need to be relocated, such as in a different control room or outside of the plant, the cables would need to be rerouted to this new site. Rerouting all of the cables is labor intensive and expensive.

To further complicate matters, the wires may need to be buried in the ground (typically below the frost line) to comply with building code requirements or simply as a precautionary measure. Burying multiple wires in the ground requires substantial excavation which is rarely inexpensive. Similarly, repairing, replacing or moving these wires also requires substantial, expensive excavation.

Alternatively, the wires may need to be suspended at a height substantially above ground level. Such suspension may require the installation and maintenance of some sort of suspension devices, such as telephone poles. These poles would be placed in and around the chemical plant. This, again, may be an expensive undertaking. Finally, with regard to hard wiring, the wires themselves are usually expensive and are prone to breaking, cracking or failing in some sort of way. Thus, it is apparent that a wireless toxic gas monitoring system is desirable. The present invention comprises such a wireless toxic gas monitoring system.

It is common to monitor gas levels around large plants. Additionally, it is not uncommon for gas monitors to be placed some distance from these large plants. Consequently, the monitors may have to transmit information a substantial distance. Moreover, because the destination of this information is often located somewhere deep within the plant, e.g., a central control room, the monitors may need to relay this information through physical objects, such as layers of concrete, steel, insulation and other building materials.

In addition to physical barriers, the monitors usually need to transmit the information through substantial interference as well. Electric equipment and communication systems existing in almost all plants create vast amounts of interference such as electromagnetic waves, for example. Thus, a wireless gas monitoring system that is able to transmit information over a substantial distance and through substantial amounts of interference is desirable. The current invention utilizes, but is not necessarily limited to, licensed radio frequencies that operate at higher powers and are therefore able to transmit over large distances and through substantial amounts of interference.

Radio telemetry has recently been used as a lower cost alternative to hard wiring the monitors to the output or control systems. However, currently such radio telemetry has been limited by technology such that each monitor must have its own radio and remote terminal unit (RTU). A typical radio telemetry system using RTU's, while reducing significant installation costs, still requires both the high cost of the RTU as well as the installation costs to wire the gas monitors to the RTU. With the advent of the current invention, the advantages of wireless toxic gas monitoring systems are realized. This is particularly true with respect to very long conduit runs, such as with perimeter monitoring applications, where the cost of the RTU and wiring the sensors to the RTU is increased by the long lengths of conduit and installation costs.

Additionally, most monitors of the related art are event triggered only. By this it is meant that the monitors only relay a signal when they detect a high level of gas. The monitors merely let you know when a threshold level of gas (such as a gas denoted "alpha") has been surpassed. For instance, if a system were set to detect 0.5 ppm of gas alpha but a dangerously high level of 20 ppm of gas alpha existed around the plant, the detector would only transmit a signal telling the controller that an amount of gas alpha above 0.5 ppm had been detected. However, the actual concentration, i.e. the dangerously high 20 ppm of gas alpha, would not be relayed back to the control room. This type of system would not provide and quantitative documentation which may be useful in any number of situations.

Thus, a wireless gas monitoring system with heightened sensitivity is desirable. By this it is meant that it would be desirable to have monitors that monitor and relay more detailed information. The current invention does just that. The monitors will not only relay the actual amount of gas detected, i.e. 20 ppm, but they may also relay operating parameters of the system such as the battery voltage, day, date, time, wind speed, weather conditions, etc. existing at the time the gas was detected.

From the foregoing it is clear that certain improvements are desired. Many of the desired improvements have been accomplished by the current invention.

The present invention contemplates a new and improved method and apparatus for wireless gas monitoring which is simple in design, effective in use, and overcomes the foregoing difficulties and others while providing better and more advantageous overall results.

SUMMARY OF THE INVENTION

The current invention is a system for wireless toxic gas monitoring with a monitoring device that eliminates the RTU by integrating the radio transmitter and making it integral with the device. Although the current invention may utilize licensed UHF radio transmissions, the device is not limited to the type of radio, whether it be land based, cellular or satellite, the strength or radio or any safety classifications.

The transmitters feature a unique method of wireless monitoring that eliminates not only the high installation costs of hardwired systems, but also the cost of wireless Remote Terminal Unit's (RTU's). A typical perimeter gas monitoring system, where the monitors are completely hardwired to the master site, costing in the neighborhood of $400,000 may only cost $200,000 if the monitors are hardwired to RTUs and the RTUs transmit via radio to the master. The current invention which has the transmitters integral with the monitors would reduce the cost of this system to approximately $100,000 by eliminating the RTU's and the associated installation costs.

One advantage of the current invention is that the licensed radio frequencies enable the current invention to operate at higher powers. This allows the monitors of the current invention to transmit information over large distances and through substantial amounts of interference.

Another advantage of the current invention is the fact that it is wireless. This permits toxic gas monitoring and installation to be performed in an inexpensive manner not requiring substantial and frequent maintenance.

Yet another advantage of the current invention is the fact that remote transmitters are integrated into the monitors of the current invention. This enables equipment, maintenance, labor, manufacturing and installation costs and expenses to be reduced.

Still another advantage of the current invention is the fact that each of the monitoring devices and the output center may comprise a transceiver. The transceiver can both transmit and receive messages. Separate transmitters and receivers are therefore not needed and costs are thereby reduced.

Another advantage of the current invention is its heightened sensitivity. Upon detection of a gas, the monitors monitor and transmit a substantial amount of detailed information.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangement of parts. A preferred embodiment of these parts will be described in detail in the specification and illustrated in the accompanying drawings, which forms a part of this disclosure and wherein.

DESCRIPTION OF THE PREFERRED EMBODIMENT

Figure 1:
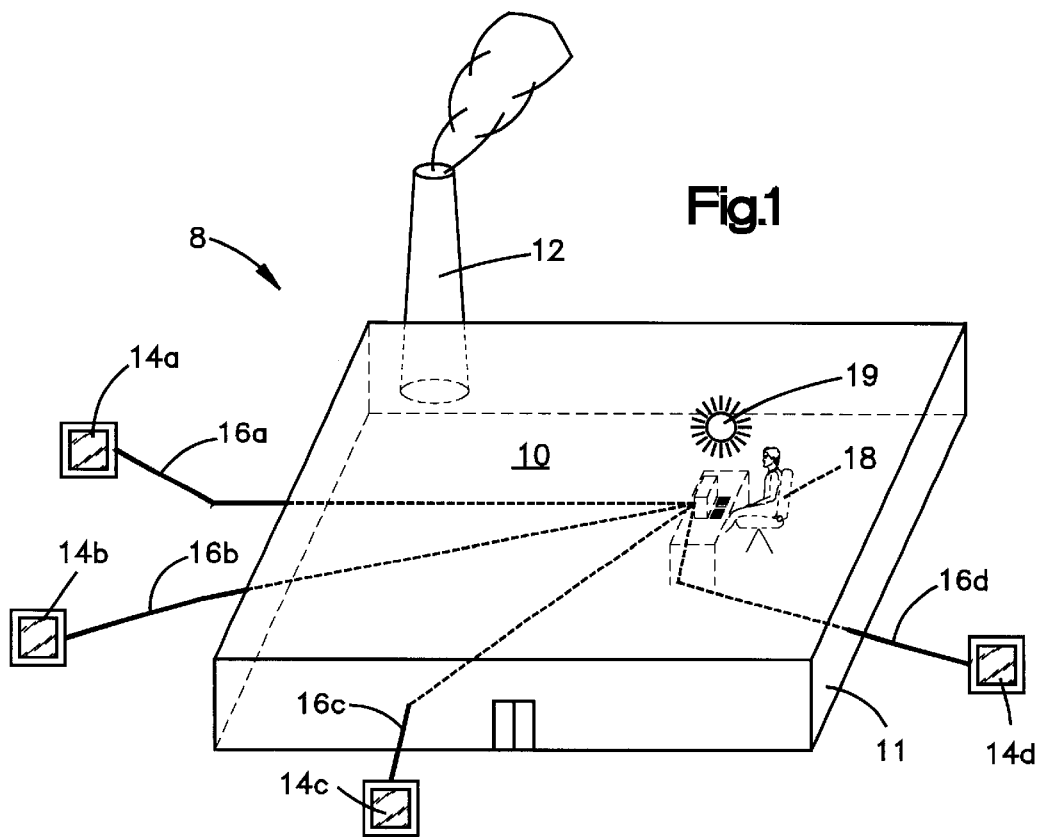
FIG. 1 shows a gas monitoring system of the related art wherein the gas monitors are hard wired to the control center of a plant.
Figure 2:
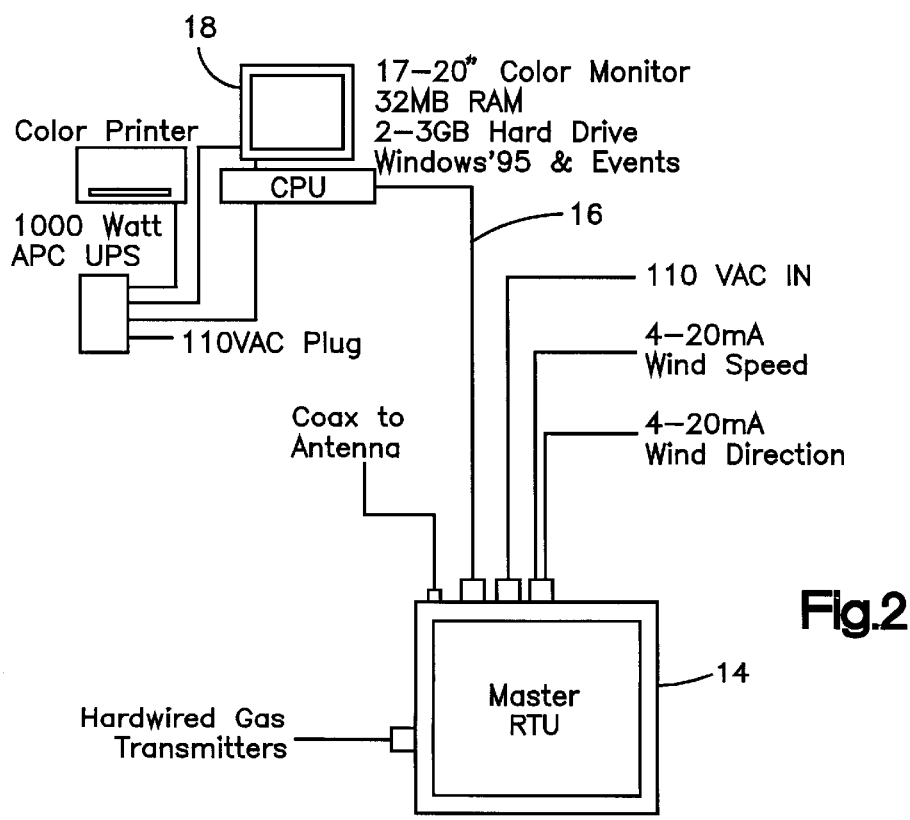
FIG. 2 is an alternative depiction of a gas monitoring system of the related art wherein the gas monitors are hard wired to the control center of a plant.

Referring now to the drawings, which are for purposes of illustrating a preferred embodiment of the invention only, and not for purposes of limiting the invention, FIG. 1 shows a chemical processing plant 10. The plant 10 is depicted as having a discharge means 12. Multiple toxic gas monitors 14a, 14b, 14c, 14d are placed around the plant 10. FIGS. 1 and 2 show the previous technology wherein each monitor 14a, 14b, 14c, 14d had to be hard wired via cables 16a, 16b, 16c, 16d to the control center 18. Should control center 18 need to be relocated at a different site, such as outside of the plant 10, the cables 16a, 16b, 16c, 16d would need to be extended to this remote site. Such a configuration and any changes to such a configuration were expensive, labor intensive and required substantial and frequent maintenance.

Figure 3:
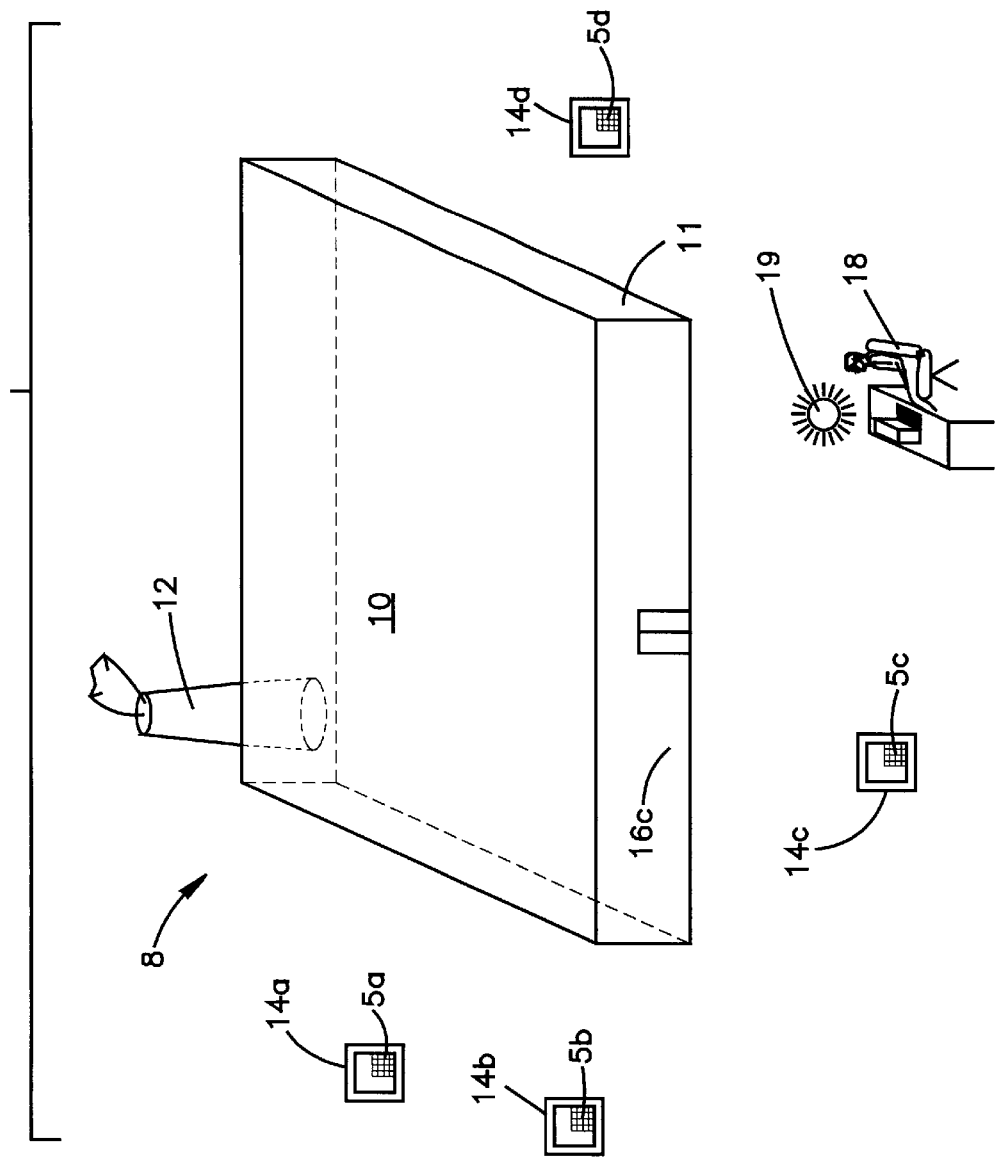
FIG. 3 shows the wireless gas monitoring system of the current invention wherein the transmitters are integral with the monitors.

FIG. 2 depicts the interconnection of some of the equipment of related art gas monitoring systems. FIG. 2 also gives some specifications on some of this equipment. Note that, in operation, the gas monitoring system 8 (FIG. 3) of the current invention may utilize much of the same equipment. However, most of the interconnection of this equipment will be by way of radio frequencies rather than wire cables 16a, 16b, 16c, 16d (FIGS. 1, 2 and 3). The inventive system disclosed herein has advantages over the related art because, in addition to having all of the hardware, software and other elements necessary to monitor around the plant, the transmitters are integral with the monitors 14. Thus, no hardwiring and RTU's are necessary.

Figure 4:
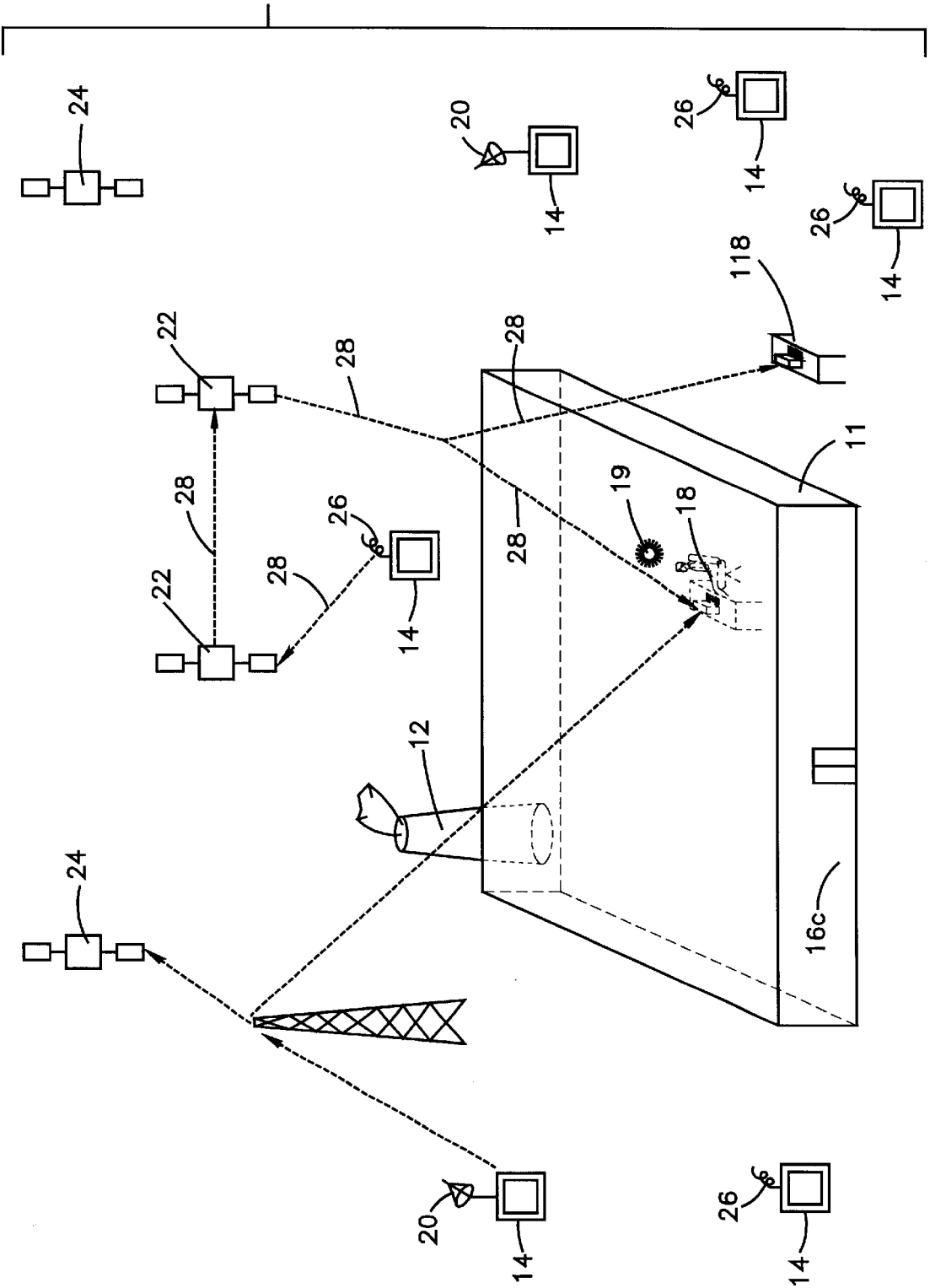
FIG. 4 shows the current invention utilizing cellular and/or low earth orbit (LEO) satellite technology.

FIG. 4 shows a chemical plant 10 with monitors 14 around the plant. Monitors 14 employing radio telemetry are depicted comprising satellite dishes 20. In the past, in order to have a wireless connection to the control center 18, each monitor 14 needed to employ an antenna more powerful than a cellular phone antenna. Additionally, these antennas needed to have a higher gain than that of a cellular phone antenna. These requirements were usually met by a remote terminal unit that sometimes included a satellite dish. Prior to the advent of low earth orbit (LEO) satellite technology, these large dishes were necessary because previous satellites were at a higher altitude and had orbits different from low earth orbit satellites 22. Because the prior satellites were at higher altitudes and had different orbits, an antenna with a higher gain, such as a satellite dish, was required for communication between the satellite 24 and the monitor 14 on the ground. These remote terminal units were bulky and expensive. Should the current invention utilize low earth orbit satellite technology, the monitors 14 need only comprise a small antenna 26 similar to a small cellular phone antenna to communicate with the low earth orbit satellites. Thus, the current invention permits an inexpensive, reliable and virtually maintenance free wireless connection to be made to the control center 18. Compared to the related art, the current invention 1 provides a substantially smaller and less expensive detection system.

When utilized in conjunction with LEO technology, the small wireless antenna 26 employed in the toxic gas monitoring devices 14 of the current invention transmit a wireless data message comprising information such as gas detected, wind speed and wind direction. The data message is transmitted to a LEO satellite 22 where it may be linked to a local gateway for validation and optimal routing to the recipient which would be the control center 18. This transmission pathway is depicted as lines 28 in FIG. 4. With this wireless technology, the control center 18 may be easily and conveniently located and relocated without the inherent difficulties of hard wiring or moving cumbersome and expensive equipment. For demonstrative purposes, FIG. 4 depicts control center 118 being located outside of plant 10.

When operating with LEO technology, a monitor 14 transmits information regarding a change in toxic gas detected by way of the low earth orbiting satellites 22 to the control center 18. This information is transmitted repeatedly as changes in readings occur. However, once the monitor 14 no longer detects toxic gas at a predetermined level, the transmitter preferably stops transmitting and waits for the next changed reading.

Additionally, the control center 18 may have the ability to transmit as well as receive data messages. For instance, the control center 18 may periodically poll each monitor 14 for supervisory purposes. Thus, each monitoring device 14 may also have the ability to receive as well as transmit wireless data messages, such as in the form of polling messages, for example.

With low earth orbit satellites, more than one monitor 14 of the wireless toxic gas monitoring system of the current invention can interactively relay data messages. Each and every one of the monitors 14 can simultaneously transmit data messages to the low earth orbit satellites and the satellites will carry through and deliver the entire data message to the control center 18. Because of this capability, low earth orbit technology offers the advantage of not missing transmissions and information.

FIG. 3 shows the preferred embodiment of the current invention that does not use satellite technology. A chemical plant 10 is shown with monitors 14*a*, 14*b*, 14*c*, 14*d* of the current invention around the plant. In this embodiment, the transmitters are integral with the monitoring devices 14. A wireless data message comprising information such as the actual amount of gas detected, battery voltage, wind speed, wind direction, etc. 36 is transmitted from the monitors 14*a*, 14*b*, 14*c*, 14*d* to the control center 18. With this wireless technology, the control center 18 may be easily and conveniently located and relocated without the hassle of hard wiring or moving cumbersome and expensive equipment. For demonstrative purposes FIG. 3 depicts control center 18 being located outside of plant 10.

Figure 5:
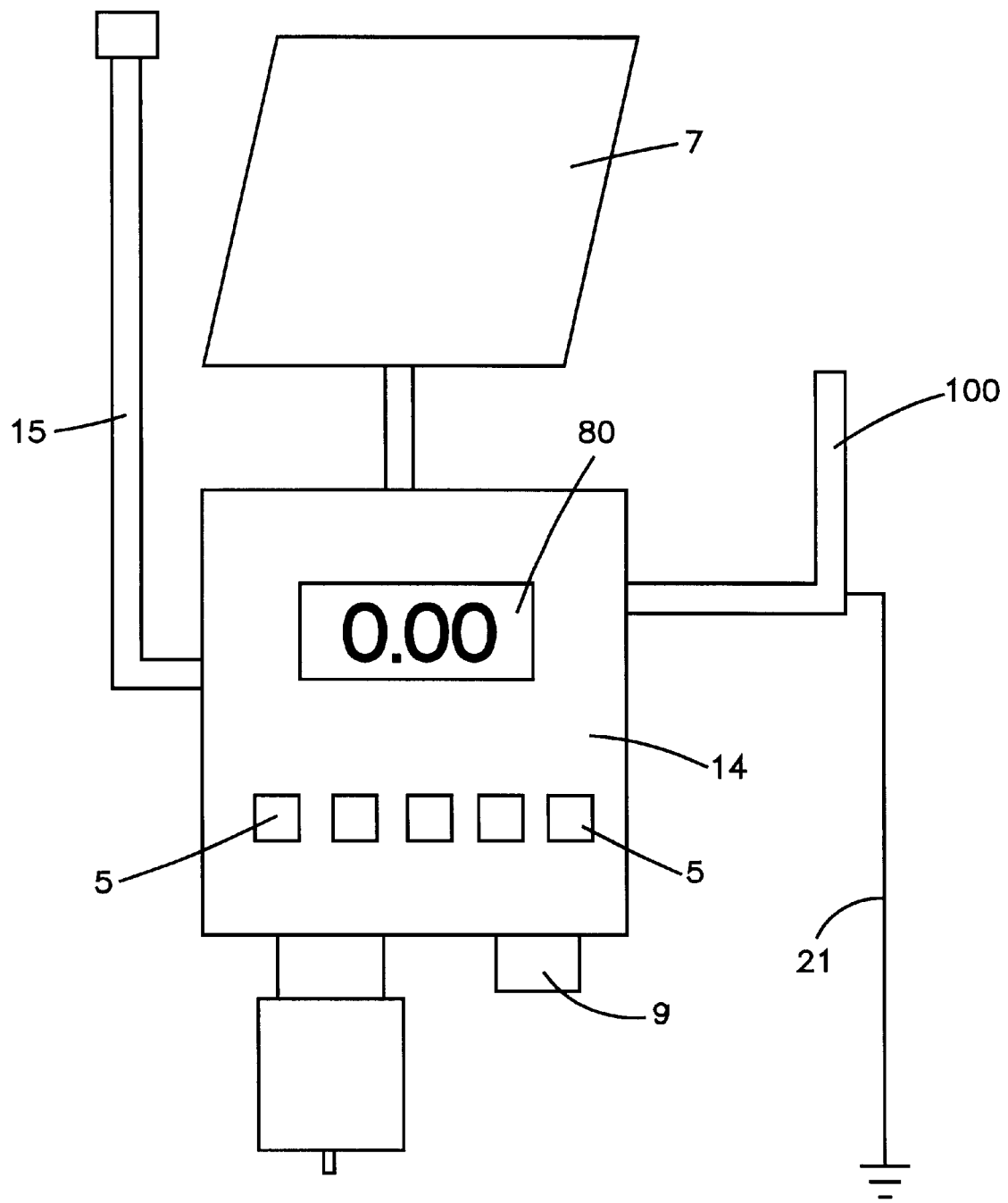
FIG. 5 and 5a shows the preferred embodiment of the current invention utilizing radio and solar technology.
Figure 5A:
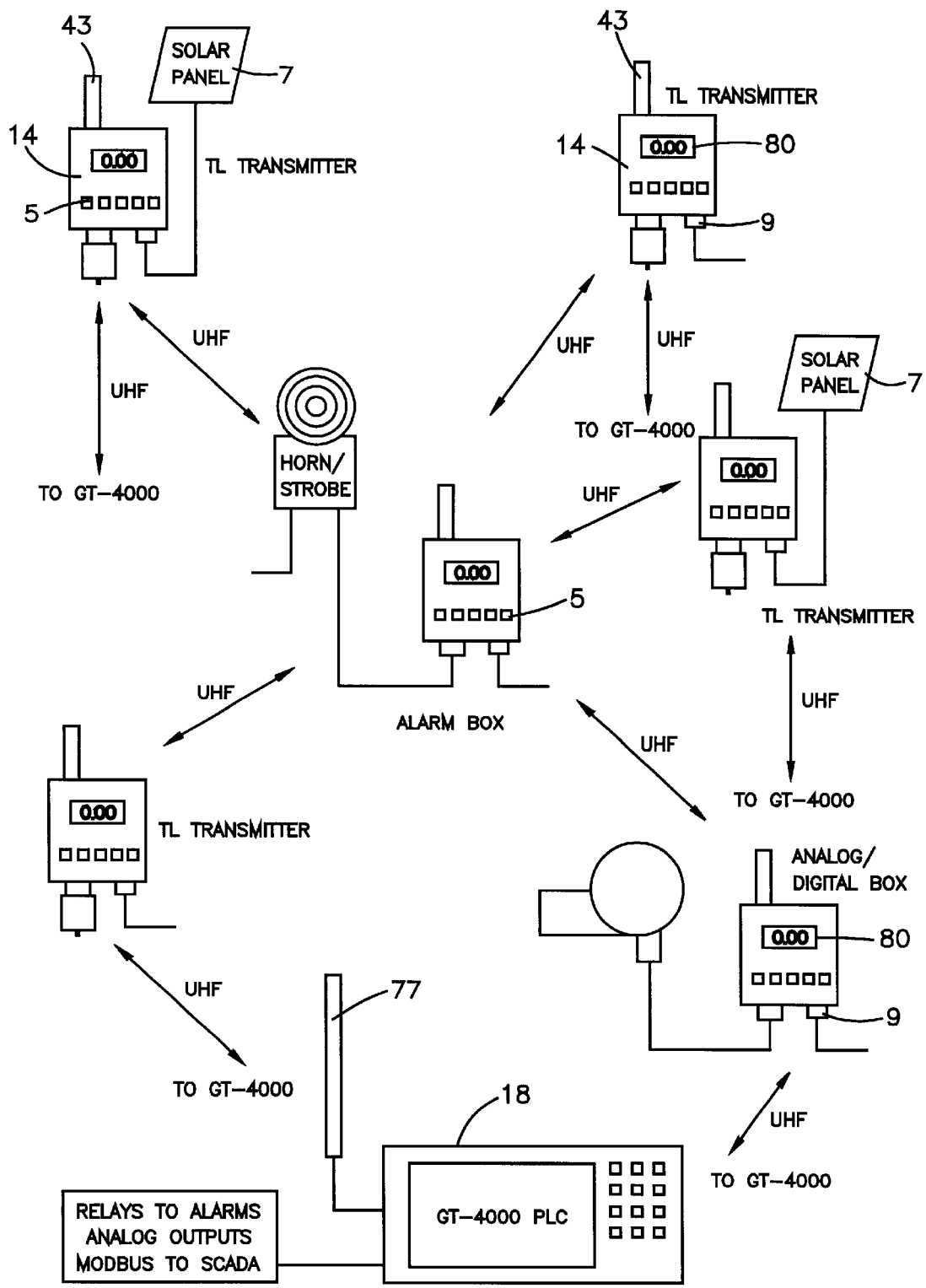

So that the system may be further wireless, applicant envisions that the monitors 14*a*, 14*b*, 14*c*, 14*d* may be solar 7 or battery 9 powered (FIGS. 5 and 5*a*) or powered by any other source of power chosen with sound engineering judgment. In the preferred embodiment, each monitor comprises a 4 amp lead acid battery capable of supporting the system a nominal operation for up to five days without power as well as a 20 watt solar panel. Additional battery power is optional. Preferably, the monitoring devices operate properly at temperature ranges between −40 degrees C. to +50 degrees C. It is also preferred that the monitors are shielded against lightning strikes through a lightning arrestor 100 combined with a copper ground rod 21 (FIG. 5). It is further preferred that the solar panel be 5 inches by 13 inches and that each monitoring device be comprised within a 6 inch by 6 inch by 4 inch housing.

With continuing reference to FIG. 3, the gas monitoring system 8 disclosed herein may operate at any frequency, but preferably utilizes licensed radio frequencies. Licensed radio frequencies provide better and more advantageous overall results than the radio frequencies used in the related art. This is because nonlicensed radio frequencies operate at lower power than licensed radio frequencies. The lower powered nonlicensed radio frequencies are unable to transmit data from the monitors 14*a*, 14*b*, 14*c*, 14*d* to the control room 18 typically located inside the plant 10. Additionally, the nonlicensed radio frequencies are unable to transmit over substantial distances or through substantial interference. The monitors 14*a*, 14*b*, 14*c*, 14*d* disclosed herein can transmit detailed information over substantial distances and through substantial amounts of interference.

The monitors 14*a*, 14*b*, 14*c*, 14*d* disclosed herein can accurately transmit information through walls 11 as well as interference in the form of electromagnetic waves, for example. These particular types of interferences and impedances are encountered in almost all gas monitoring applications. This is because the destination of the information transmitted by the monitors 14*a*, 14*b*, 14*c*, 14*d* is usually located somewhere within the plant 10. Typically, the control room 18 is centrally located somewhere deep within the plant 10. Consequently, the monitors 14*a*, 14*b*, 14*c*, 14*d* must transmit the data through physical barriers of the plant 10 such as concrete and steel walls 11. Additionally, this information must successfully traverse interference created by electric equipment and communication systems. Such interference typically presents itself in the form of electromagnetic waves which exist within virtually all plants 10.

The licensed radio frequencies disclosed herein may be obtained by way of application to the Federal Communications Committee "FCC." Applicant notes that a particularly useful bandwidth of licensed radio frequencies would be between 450–470 megahertz "mHz". Preferably, the current invention operates within this bandwidth. Preferably, the transmitters 42 that are integral with the monitoring devices 14 comprise an up to a 5 Watt 450–470 mHz (UHF) radio transmitter. This eliminates the need for wiring to a Remote Radio Terminal Unit (RTU), thereby significantly reducing costs.

Regardless of the frequency used, the current invention, even without the use of satellite technology, will not miss transmissions. This is because each monitoring device 14 will very rapidly transmit its readings to an output center. Because these transmissions occur so often, there is insufficient time for data readings to accumulate between transmissions.

Preferably, the monitoring devices 14 comprise more than one sensor 38 to sense various gasses. In the preferred embodiment, the gas sensors 38 are electrochemical, infrared or catalytic gas sensors. Some of the sensors may operate in the range of 4 mA to 20 mA. Preferably, the gas detection system 8 disclosed herein comprises means 5 (FIG. 5) to interface with each monitor 14a, 14b, 14c, 14d (FIG. 3). Preferably, this is an easily accessible keypad 5a, 5b, 5c, 5d on the face of each monitor 14a, 14b, 14c, 14d. This keypad 5a, 5b, 5c, 5d allows the monitoring devices to be manipulated. For instance, they may enable the monitoring devices 14a, 14b, 14c, 14d to be programmed for the particular type of gas to be monitored for as well as the level of this gas which causes the monitors to start transmitting information.

Figure 6:
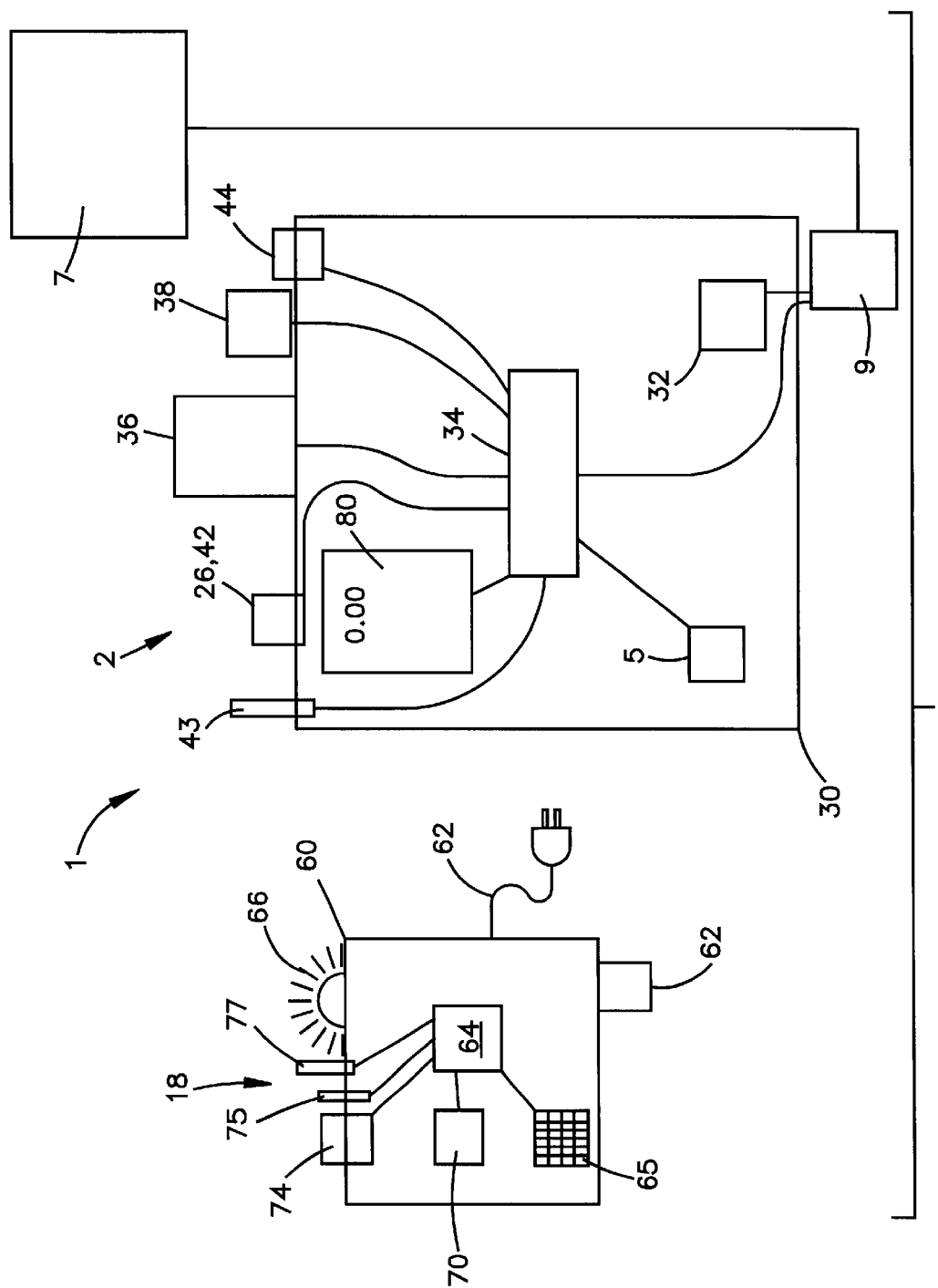
FIG. 6 shows another preferred embodiment of a monitoring device of the current invention.

Preferably, each monitoring device 14 comprises a display 80 (FIG. 5). Each device can be configured so that any number of readings taken by the device are displayed on the display 80. With reference to FIG. 6, each monitoring device also comprises a microprocessor 34 for driving the display 80 and causing the appropriate reading to be displayed on the display 80. The microprocessor 34 also enables a user to interface with the device via the interface means 5. Preferably, the microprocessor links the display 80 and the interface means 5 so that the display 80 is useful in assisting a user to interface with the monitoring device 14. It is further preferred, that the microprocessor 34 monitors sensor readings and initiates and controls transmissions. Optionally, the microprocessor may cause the monitoring devices to periodically transmit polled data readings.

Additionally, it is preferred that the monitoring devices 14a, 14b, 14c, 14d are reprogrammable. By this it is meant that the monitors 14a, 14b, 14c, 14d may be used time and again for the detection of different gases. It is further preferred that via the interface means 5 selective monitoring may be accomplished. By this it is meant that the particular condition(s) to be monitored for may be selected and the monitoring devices 14a, 14b, 14c, 14d calibrated and configured accordingly. It is preferred that the monitoring devices can at least monitor for chlorine, ammonia, hydrogen fluoride, hydrogen cyanide, phosphene, fluorine, chlorine dioxide, phosgene, carbon monoxide, ozone, diborane, methyl mercaptan, hydrogen sulfide, sulfur dioxide, hydrazine, silane and germane at a plurality of concentrations. An alternative embodiment within the scope of the invention has a receiver 44 connected to the microprocessor 34. The receiver 44 allows remote transmissions to be received by the monitoring device 14. This may allow, for example, the operating parameters of the monitoring device to be reprogrammed from a remote location.

For optimum performance, simplicity and efficiency, it is preferred that the transmitter 42 and receiver 44 are integrated into a single component known as a transceiver 43 (FIG. 6). In this fashion, each monitoring device 14 is very compact and is literally a remote transmitting unit as well as a remote receiving unit. The monitoring devices 14 then do not require remote terminal units RTU's to transmit or receive data messages. The cost of toxic gas monitoring is thereby significantly reduced.

In operation, preferably the monitors "sleep" unless a change causes them to transmit. By this it is meant that the monitors do not transmit data unless a preprogrammed level of a particular gas is detected or upon a battery voltage change or in reply to a transmission from the master site(s). Once this event occurs, the monitors begin to transmit data. The monitors 14a, 14b, 14c, 14d transmit information regarding changes in gas detected. This information is transmitted repeatedly as changes in readings continue. However, once the monitors 14a, 14b, 14c, 14d no longer detect gas at a predetermined level, the monitors 14a, 14b, 14c, 14d again rest and wait for the next changed reading. Upon a subsequent changed reading that exceeds the predetermined threshold level, the monitors once again begin to transmit information. According to another embodiment of the invention, the control center 18 may periodically poll each monitor 14a, 14b, 14c, 14d for supervisory purposes.

The monitors of the current invention allow the transmission of information which may be quantified. By this it is meant that the monitors transmit detailed information. The monitors transmit not only the actual amount of gas detected but also the status of important surrounding circumstances. For instance, this information may include the parts per million (ppm) of gas detected, explosion limit levels, battery voltage (voltmeter 32), alarm statuses, date, time, wind speed, wind direction (weather sensing means 36), etc. existing at the time the gas was detected.

According to another embodiment of the invention, upon detection of a toxic gas, usually at a predetermined level, the system may sound an alarm box 19 (FIG. 3). The alarm may be sounded alone or in addition to relaying the aforementioned information to the output center 18. Alternatively, the master site may only be the alarm boxes rather than a output center 18. Additionally, alarms 19 could also be on the monitors 14 and/or in the control room 18. Preferably, the alarm box is a 5 Watt UHF radio receiving device providing 3 amp to 10 amp rated relays that are synchronized to the alarm settings of the transmitters.

Preferably, the output center 18 has a receiver 74 for receiving transmissions from a monitoring device 14. The output center 18 also has a housing 60, microprocessor 64, and power means 62 for powering the output center. Additionally, the output center 18 has a display 70 and interface means 65. Preferably, the microprocessor 64 connects the receiver 74, display 70, interface means 65 and signaling means 66 for producing a signal. The signal may be an audible or visual signal that signal the detection of a certain gas.

As mentioned above, the output center 18 may periodically poll each monitoring device 14, such as for supervisory purposes, for example. Thus, as with each monitoring device 14, the output center 18 preferably can transmit as well as receive data messages. To effect this the output center 18 may have a transmitter 75 operatively connected to the microprocessor 64. However, for optimum compactness and operating efficiency, again as with each monitoring device 14, the output center 18 has a single transceiver 77 that both transmits and receives data messages (FIG. 6). This eliminates the need for the output center 18 to have both a transmitter 75 and a receiver 74.

Preferably, each monitoring device 14 has its own housing 30 and site address with respect to the rest of the system. This address distinguishes one monitoring device from another. Preferably, each monitor can be tied into other detection systems by providing an ASCII formatted RS232 signal to a DCS. Since many DCS systems require Modbus for their driver, the Master RTU is often directly compatible. Analog outputs for each transmitter can be provided through the use of an analog output expansion card.

Reliable and appropriate sensor technology will be incorporated into the system. A couple of sensor manufacturers, with whose products the current invention performs optimally, are Sensoric and GmbH. Some benefits of the sensors used in the current invention are: no temperature effects, no humidity effects, no periodic zeroing required, no background current, greater chemical selectivity, no drying out, no taking on moisture, no costly recharges or refilling of electrolyte.

Specifications regarding the preferred embodiment of the current invention are as follows:

| | |
|---|---|
| Housing | Nema-4X Optional Explosion Proof Version) |
| Temperature Range | −40° C. to +50° C. |
| Humidity Range | 0–100% RH |
| Power Options | 115/220 VAC or 12 VDC Solar Powered |
| Power Consumption | 40 mA Nominal, 1000 mA during transmission |
| Internal Battery | 12 VDC, 4 Amps |
| Radio Power | 2 watts or 5 watts |
| Antenna Gain | 3 db |
| Radio Frequency | UHF Licensed, Provided by Gastronics |
| Frequency Adjust | Crystals |
| Microprocessor | 32 bit |
| Analog Resolution | 16 bit |
| Keypad Settings | Trigger on Change, Drop Out, Analog Filtering, STEL/Hi/HiHi Alarms, Remote Site Address, Master Site(s) Address, Alarm Box Site Address |
| Jumper Settings | Display Resolution, Sensor Type, Sensor Range |

The invention has been described with reference to the preferred embodiment. Obviously, modifications and alterations will occur to others upon a reading and understanding of the specification. For instance, the current invention may be used to monitor for other than toxic gases and at other than chemical processing plants. And, applicant anticipates that the system will comprise other than four monitors and/or four configuration means. It is intended by applicant to include all such modifications and alterations.

Having thus described the invention, it is now claimed:

1. A method of monitoring atmospheric conditions, comprising the steps of:

providing an air-monitoring unit having a weather-sensing means for use in sensing a plurality of ambient atmospheric conditions, said weather-sensing means providing a first quantitative output; gas-sensing means for use in sensing levels of associated toxic gases, said gas-sensing means providing a second quantitative output; wireless communication means for communicating said first and second quantitative output to an associated control center; power-supplying means for supplying power to said air-monitoring unit; and, logic controlling means having at least a first threshold value, said logic-controlling means operatively connected said weather and gas-sensing means and said wireless communication-means for use in enabling said wireless communication-means to transmit said first and second quantitative output;

sensing levels of said associated toxic gases and said ambient atmospheric conditions;

comparing said second quantitative output of said gas-sensing means to said threshold values; and, selectively enabling said wireless communication-means to transmit said first and second quantitative output to said associated control center.

2. The method of claim 1, wherein the step of selectively enabling said wireless communication means occurs only while said second output surpasses said threshold value.

3. An air-monitoring unit for monitoring atmospheric conditions, comprising:

weather sensing means for use in sensing a plurality of ambient atmospheric conditions, said weather sensing means providing a first quantitative output;

gas-sensing means for use in sensing levels of toxic gases, said gas-sensing means providing a second quantitative output;

wireless communication means for use in communicating said first and second output to an associated control center;

power-supplying means for independently supplying power to said air-monitoring unit; and, logic-controlling means for use in operatively controlling said air-monitoring unit, said logic-controlling means stores at least a first toxic gas level value for use in comparing said value to said second output, and wherein said logic-controlling means enables said wireless communication means to communicate said first and second quantitative outputs to said associated control center based on comparing said value with said second quantitative output.

* * * * *